United States Patent [19]

Huvé

[11] 4,344,947

[45] Aug. 17, 1982

[54] USE OF ISOPROPYLAMINOPYRIMIDINE IN THE CHEMOTHERAPY OF MUSCULAR DYSTROPHY, MYOPATHY AND MYTONIA

[75] Inventor: Pierre M. Huvé, Paris, France

[73] Assignee: Societe d'Etudes de Produits Chimiques, France

[21] Appl. No.: 201,709

[22] Filed: Oct. 29, 1980

[30] Foreign Application Priority Data

Nov. 2, 1979 [CA] Canada ................................. 339073

[51] Int. Cl.³ ........................................... A61K 31/505
[52] U.S. Cl. .................................................... 424/251
[58] Field of Search ......................................... 424/251

[56] References Cited

U.S. PATENT DOCUMENTS 4,073,895  2/1978  Esanu ................................. 424/251

*Primary Examiner*—Stanley J. Friedman
*Attorney, Agent, or Firm*—Thompson, Birch, Gauthier & Samuels

[57] ABSTRACT

A method for the chemotherapy of muscular dystrophy which includes administrating an effective amount of 2 isopropylaminopyrimidine.

4 Claims, No Drawings

USE OF ISOPROPYLAMINOPYRIMIDINE IN THE CHEMOTHERAPY OF MUSCULAR DYSTROPHY, MYOPATHY AND MYTONIA

BACKGROUND AND BRIEF SUMMARY OF THE INVENTION

The present invention is directed to a new use of an existing compound. U.S. Pat. No. 4,073,895 relates to the use of a substituted salt of 2 aminopyrimidine. This patent in fact teaches that a particular salt of 2 aminopyrimidine, namely 2 isopropylaminopyrimidine orthophosphate (IAPP), is useful as an active agent for the treatment of neuropathies. Although this use is known, the particular efficacy of the salt against muscular dystrophy has yielded unexpected and superior results.

The invention broadly comprises a method for the chemotherapy of muscular dystrophy, which comprises administering an effective dosage of 2 isopropylaminopyrimidine or therapeutically acceptable salts of the same or the hydroxylated and oxygenated metabolites thereof.

DESCRIPTION OF THE PREFERRED EMBODIMENT

In the following discussion, the specific compound used for testing is 2 isopropylaminopyrimidine orthophosphate as disclosed in U.S. Pat. No. 4,073,895, which patent is hereby incorporated by reference in its entirety in this application.

EXAMPLE I

The dystrophic chicken homozygote was used for monitoring chemotherapy of muscular dystrophy. This particular animal line inherits dystrophy in a form as close as possible in causation and course to human dystrophy and also permits quantitative assessment of progress of the disease by several independent methods.

The compound IAPP was tested on dystrophic New Hampshire chickens, line 413, and Imperial College (London, England) sub-line of the original Davis, University of California strain. The chickens are homozygous for muscular dystrophy, the disease appearing with 100% incidence.

Chemotherapy was assessed by application of seven different parameters: physical tests of muscular disability, namely the flip test and wing apposition (W.A.) measurements; biochemical assays of serum and muscle enzyme levels of creatine phosphokinase (CPK), pyruvate kinase (PK) and acetylcholinesterase (AChE); and histologial comparisons of treated and untreated muscle. Toxicity studies (weight loss, etc.) were also used. A very comprehensive profile of the drug was thus obtained which related to all the known, highly characteristic features of the disease which are applicable to both the animal model and the human.

DESCRIPTION OF TESTS

1. The Flip Test

The animal is placed on its back in the supine position. The number of times it is able to rise, out of five attempts, is known as the flip number (FN). The normal chicken invariably scores 5 (out of 5 attempts), whereas in an untreated dystrophic chicken, the number declines to zero in 6–8 weeks. The test is performed once every seven days; more frequent assessment introduces an exercise factor and is not recommended.

2. Wing Apposition Measurements

This can be defined as the minimum separation in cm to which the two wing tips can be passively raised, providing a measure of the characteristic loss in flexibility of the wing muscle-tendon system. The test is performed once weekly. In dystrophic birds, WA changes after the first three weeks of life from 0 cm (wings raised and touching) to about 18 cm at 3 months, (wings stiff and can barely be raised). The normal controls maintain a score of 0 cm throughout.

3. Plasma CPK

Plasma CPK rises dramatically in the dystrophic chicken as it does also in the human disease. The normal chicken has 200–300 U/l CPK, compared to about 20,000 U/l in the untreated dystrophic chicken at its peak. It rises to these high levels over a period of two months and is, therefore, a significant index of the disease.

4. Plasma PK

A massive rise in this enzyme level also occurs in the dystrophic chicken compared to the normal control, as it does in the human disease.

5. Plasma AChE

The elevation of this enzyme in the dystrophic chicken occurs from 8 days and reaches a plateau at 100 days, compared to the normal animal where the levels continue to decline slowly.

6. Histopathology

Muscle fibre area increase greatly in the dystrophic chicken as does the range of fibre area sizes. Nuclei become displaced peripherally and both features can be measured quantitatively and compared with normal controls.

7. Forms of AChE in the Muscle

Toxicity—Weight measurements are taken weekly, weight loss, diarrhea or any other symptoms are noted. No drugs have yet been described for dystrophy with a beneficial effect without an accompanying weight loss.

The drug was administered daily in water, injected intra-peritoneally, the amount being adjusted on a weekly basis according to the animal's weight.

Median Lethal Dose

Initial single injections of IAPP at 50 mg/Kg and 100 mg/Kg produced no weight loss over 7 days, nor any other toxic symptoms.

|  | Experiment No. 1 |
|---|---|
| Dosage: | 30 mg/Kg |
| No. Treated Animals | 8 |
| No. Control Animals | 7 |
|  | Experiment No. 2 |
| Dosage: | 40 mg/Kg |
| No. Treated Animals | 7 |
| No. Control Animals | 7 |
|  | Experiment No. 3 |
| Dosage: | 70 mg/Kg |
| No. Treated Animals | 10 |
| No. Control Animals | 10 |

Experiment No. 1

Dosage at 30 mg/Kg IAPP showed no significant differences between the treated and dystrophic control animals in the parameters measured.

Experiment No. 2

Results of dosage at 40 mg/Kg IAPP are set forth below in Table I. The results showed a significant effect of IAPP on all parameters measured. CPK, PK and AChE enzyme levels were reduced dramatically, although the effect was declining at the end of the 10-week experiment. The Flip number and wing apposition measurements gave a valuable measure of the bird's immediate physical condition, and showed a significant improvement in the treated group.

Experiment No. 3

Results of dosage at 70 mg/Kg IAPP are set forth below in Table 2. The results after 4 weeks' treatment showed a similar effect to treatment at 40 mg/Kg at this stage. Both experiments appear to show that the drug is effective at an early age. The higher dosage also produces detectable toxicity as evidenced by weight loss, but this is still moderate.

Significant effects are reached on the parameters measured with little or no concomitant toxic effects.

injected to yield a final concentration of 25 mg/ml or 2.5 mg/ml.

| Treatment | No. Eggs | No. Hatched |
|---|---|---|
| 412 Normal: | | |
| control | 12 | 11 |
| drilled control | 12 | 11 |
| saline injected controls | 12 | 9 |
| 2.5 mg/ml | 12 | 6 |
| 25 mg/ml | 12 | 2 |
| 413 Dystrophic: | | |
| control | 12 | 9 |
| drilled control | 12 | 10 |
| saline injected controls | 12 | 9 |
| 2.5 mg/ml | 12 | 0 |
| 25 mg/ml | 12 | 0 |

The dystrophic (413) eggs are somewhat less fertile than the normal (412). In these experiments, it was observed that typical percentage hatching in the control eggs (i.e., most of the normal hatch and usually one or two fewer eggs hatch from the dystrophic eggs from

TABLE I

EXPERIMENT 2 - IAPP - 40 mg/KG

| Day | *% Weight Change | % CPK Change | % PK Change | % AChE Change | FN Treated | FN Control | WA Treated | WA Control |
|---|---|---|---|---|---|---|---|---|
| 7-13 | −0.04 | −8 | | | 4.9 | 4.5 | 0 | 0 |
| 14-20 | −0.07 | −46 | −38 | | 5.0 | 4.8 | 0 | 0 |
| 21-27 | −0.07 | −21 | −57 | | | | 0 | 0 |
| 28-34 | −0.15 | −59 | −60 | | | | 0 | 0 |
| 35-41 | −0.08 | −57 | −48 | | 5.0 | 2.8 | 0 | 2.1 |
| 42-48 | −0.04 | −72 | −58 | −55 | | | 2.3 | 4.7 |
| 49-55 | −0.04 | −47 | −49 | | 4.5 | 2.0 | | |
| 56-62 | −0.05 | −47 | −42 | | 3.8 | 1.4 | 2.9 | 5.7 |
| 63-71 | −0.01 | −32 | −41 | | 2.3 | 0.9 | 6.1 | 7.5 |

*All "% change" values show the mean percentage gain (+) or loss (−) in value of the treated animals compared to the untreated dystrophic controls. All values are the mean of the group.

TABLE II

EXPERIMENT 3 - IAPP - 70 mg/Kg

| Day | *% Weight Change | % CPK Change | % PK Change | % AChE Change | FN Treated | FN Control | WA Treated | WA Control |
|---|---|---|---|---|---|---|---|---|
| 7-13 | 0 | | | | — | — | | |
| 14-20 | −2 | | | | 5 | 5 | 0 | 0 |
| 21-27 | −3 | −51 | −32 | | 5 | 4.8 | 0 | 0 |
| 28-34 | −9 | −53 | −65 | | 5 | 5 | 0 | 0 |

EXAMPLE II

IAPP Injected into Normal and Dystrophic Eggs

Fertilized normal and dystrophic eggs were either injected with IAPP before incubation or after three days incubation. The concentrations of IAPP used in these studies were 2.5 mg/ml and 25 mg/ml solubilized in "Salts 25" solution which had previously been used in other studies injecting drugs into the yolk of avian eggs. The rationale for using these concentrations of IAPP was based on the assumption that the drug would disperse evenly throughout the yolk and would be slowly metabolized during embryonic development. The eggs were carefully drilled at one end so as to barely remove a small portion of the outer shell. Controls, drilled only controls, saline injected controls, and two different concentrations of IAPP were tested. Essentially, no differences were observed between injecting the eggs immediately upon arrival or after three days incubation and all results will be pooled in the table. Concentrations of IAPP were made so that 0.1 ml of drug was Davis, Calif. which can cause a bit of trauma to the fertilized eggs. The saline only and drilled only controls fell within the range expected considering other investigators' experiences using these techniques. Even though a few of the normals hatched that were IAPP injected, absolutely none of the dystrophic IAPP injected eggs hatched. Only one of the dystrophic eggs that had been injected with 2.5 mg/ml of IAPP showed any sign of development, but this chick never hatched. The control strains that hatched from the IAPP injections appeared normal by all criteria tested.

IAPP Injected into 3-Day Old Normal and Dystrophic Chickens

All chickens were injected with 50 mg/kg IAPP weight approximately every second or third day.

The results are outlined below:

A—control-injected with PBS;
B, C, D—experimental-injected with 50 mg/kg IAPP.

| | | WEIGHT IN GRAMS | | | | | | | | | |
|---|---|---|---|---|---|---|---|---|---|---|---|
| Day: | | 1 | 4 | 7 | 9 | 11 | 14 | 16 | 17 | 20 | 22 | 25 |
| Dystrophic | A | 38.8 | 42.9 | 51.7 | 50.8 | | | | | | | |
| 413 | B | 48.3 | 51.2 | 56.7 | 58.1 | | | | | | | |
| | C | 36.9 | 44.4 | 49.9 | 45.2 | 53.2 | 77.4 | 90.5 | 104.8 | | | |
| | D | 44.5 | 51.2 | 59.8 | 56.5 | 65.4 | 93.7 | 115.1 | — | 161.3 | 210.2 | 240.7 |
| Normal | A | 49.6 | 59.1 | 74.9 | 76.1 | | | | | | | |
| 412 | B | 51.3 | 55.8 | 67.6 | 68.1 | | | | | | | |
| | C | 50.8 | 59.9 | 67.8 | 67.7 | 76.4 | 111.8 | 139.0 | 150.2 | | | |
| | D | 52.6 | 60.5 | 67.7 | 67.7 | 76.6 | 112.8 | 139.6 | — | 191.5 | 246.4 | 273.4 |

RESULTS

1. Weight Gain

There did not appear to be a toxic side effect of the IAPP injected chickens.

2. Flip Test (25 flips)

Both the normal and dystrophic drug injected chickens were able to pass the flip test. The exception to 25 flips was that the 413D experimental animal on day 25 fatigued after 19 flips while the 412D did not fatigue. This may have been due to the lack of daily injections.

3. Culture Experiments

Essentially, these experiments were divided into three subgroups, taken from the previous table:

Subgroup A—413A, 413B, 412A, 412B.

All were sacrificed after 4 injections and muscle explants placed in culture.

Subgroup B—413C, 412C.

All were sacrificed after 8 injections and muscle explants placed in culture.

Subgroup C—413D, 412D.

All were sacrificed after 10 injections and muscle explants placed in culture.

4. Culture Conditions

All explants were placed in CMRL culture medium containing 5% horse serum, 15% fetal bovine serum and 1% antibiotics and allowed to grow for 5-7 days before being fixed and observed for the presence or absence of microtules. No IAPP was added to the culture medium during the 5-7 days in culture.

5. Microtubule Results

| | % Full Complexes Microtubules |
|---|---|
| Subgroup A | |
| 413A dyst. | 31% |
| 413B dyst. + IAPP | 58% |
| 412A normal | 86% |
| 412B normal + IAPP | 73% |
| Subgroup B | |
| 413C dyst. + IAPP | 60% |
| 412C normal + IAPP | 76% |
| Subgroup C | |
| 413D dyst. + IAPP | 74% |
| 412D normal + IAPP | 80% |

Some dystrophic 413 chickens appeared normal after 28 days of dilantin injections but explants from these animals did not have their microtubule defect corrected.

Effect of IAPP on Normal and Dystrophic Explants in Cell Culture

In these experiments 2 week and 3 week normal and dystrophic chickens (that had no previous injections with IAPP) were sacrificed and skeletal and cardiac explants were placed in culture with 0.5 mg/ml IAPP added. The pooled results of these experiments are as follows:

| | % Full Complexes of Microtubules |
|---|---|
| 412 normal controls | 75% |
| 413 dystrophic skeletal control | 23% |
| 413 dystrophic skeletal + IAPP | 38% |
| 413 dystrophic cardiac control | 36% |
| 413 dystrophic cardiac + IAPP | 43% |

Effects of IAPP on Human Blood Cells in Culture

These results suggest that dystrophic cells in culture contain reduced staining of microtubules which then appears to normalize upon incubation in IAPP.

Human monocytes from patients with Duchenne's muscular dystrophy do not spread out (become as flat) as normal cells when cultured for 5-7 days. In the experiments adding IAPP to such cultures the preliminary results are as follows:

| | % Flat Cells |
|---|---|
| Normal monocytes (six individuals) | 61.3% |
| Dystrophic monocytes (six individuals) | 36.2% |
| Carrier monocytes (six individuals) | 35.3% |
| Dystrophic monocytes + IAPP (six individuals) | 45.1% |
| Carrier monocytes + IAPP (six individuals) | 50.0% |
| Dystrophic monocyte + dibutyl c-GMP (one individual) | 52.0% |

Based on Examples I and II, a minimum concentration of 40 mg/Kg was found effective. An upper limit would be that amount where undesirable side effects occur such as weight loss due to toxicity (Example II 70 mg/Kg).

The disclosed compound is applicable for the treatment of physiological disorders directly or indirectly linked to the muscular neurotransmission; this would include myopathy of endocrine origin, myotonia and muscular dystrophy, including inherited (with and without myopathy) and acquired (toxic, infectious, immunological or from dietary origin).

The preferred embodiment of the invention has been described in reference to a therapeutically acceptable salt of a substituted 2-aminopyrimidine. The following salts derived from a substituted 2-aminopyrimidine are also considered within the scope of the invention.

TABLE III

| Name | Solvent (1) | Melting Point | Formula |
|---|---|---|---|
| methane sulfonate | E/A | 92° | $C_8H_{15}N_3O_3S$ |
| p-toluene sulfonate | E | 155° | $C_{14}H_{19}N_3O_3S$ |
| camphosulfonate | E | 130° | $C_{17}H_{27}N_3O_4S$ |
| succinate | E/A | 134° | $C_{11}H_{17}N_3O_4$ |
| fumarate | E/A | 230° | $C_{11}H_{15}N_3O_4$ |
| maleate | E/A | 73° | $C_{11}H_{15}N_3O_4$ |
| bromo furoate | E | — | $C_{12}H_{14}BrN_3O_3$ |
| nitro furoate | E | 112° | $C_{12}H_{14}N_4O_5$ |
| nicotinate | E/A | 220° | $C_{13}H_{16}N_4O_2$ |
| benzoate | E | — | $C_{14}H_{17}N_3O_2$ |
| cyclohexane carboxylate | E | — | $C_{14}H_{23}N_3O_2$ |
| phenyl acetate | E | — | $C_{15}H_{19}N_3O_2$ |
| cinnamate | E | — | $C_{16}H_{19}N_3O_2$ |
| aspartate | water | >260° | $C_{11}H_{18}N_4O_4$ |
| anthranilate | A | 62° | $C_{14}H_{18}N_4O_2$ |
| amino-4-phenylacetate | A | 208° | $C_{15}H_{20}N_4O_2$ |
| inosinate | water | 120° | — |
| orthophosphate diacide | E/A | 120° | $C_7H_{14}N_3O_4P$ |
| D—tartrate | MeOH | 110° | $C_{11}H_{17}N_3O_6$ |
| theophylline acetate | Water/EtOH | >260° | $C_{16}H_{21}N_7O_4$ |

A = ethyl alcohol
E = ethyl ether

It is possible that the salt used, IAPP, may be metabolized when absorbed in the host system under examination. The IAPP may be either hydroxylated or oxydated and the following formulaes are believed to represent possible metabolites:

hydroxylated

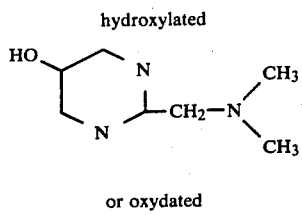

or oxydated

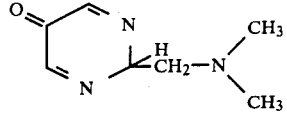

A specific salt of a substituted 2-aminopyrimidine $C_4H_5N_3$ has been disclosed. Other pyrimidine compounds, their salts and metabolites may be used, such as 2 amino and 4 aminopyrimidine; $C_4H_5N_3O_2$ (2 amino 4, 6 dihydroxypyrimidine; 6 amino 2, 4 dihydroxypyrimidine); $C_6H_9N_3$ (2 amino 4, 5 dimethylpyrimidine and 4 amino 2, 6 dimethylpyrimidine and 6 amino 4, 5 dimethylpyrimidine); $C_5H_7N_3$ (2 amino 4 methylpyrimidine, 2 amino 5 methylpyrimidine, 4 amino 2 methylpyrimidine, 4 amino 5 methylpyrimidine and 6 amino 4 methylpyrimidine); $C_4H_4N_4O_2$ (2 amino 5 nitropyrimidine); $C_9H_{14}ClN_3$ (2 chloro 4 (diethylamino) 6 methylpyrimidine); $C_5H_4Cl_2N_2$ (2, 4 dichloro 5 methylpyrimidine, 2,4 dichloro 6 methylpyrimidine); $C_4H_4N_2O \cdot HCl$ (2 hydroxy pyrimidinehydrochloride); $C_5H_7N_3$ (2 methylpyrimidine); $C_5H_6H_7$ 4 (methyl amino) pyrimidine; uracil and cytosine.

Having described my invention, what I now claim is:

1. A method for the chemotherapy of muscular dystrophy, myopathy and myotonia and/or muscular neurotransmission which comprises:
   administering by injection to an animal afflicted with a condition associated with muscular dystrophy, myopathy, myotonia and/or muscular neurotransmission 2 isopropylaminopyrimidine or therapeutically acceptable salts of the same in an amount effective to improve said condition.

2. The method of claim 1 wherein the animal is a human.

3. The method of claims 1 or 2 wherein one therapeutically acceptable salt is 2 isopropylaminopyrimidine orthophosphate.

4. The method of claim 3 wherein the condition is muscular dystrophy.

* * * * *